(12) United States Patent
Ray et al.

(10) Patent No.: US 11,980,825 B2
(45) Date of Patent: May 14, 2024

(54) DYNAMIC AND VARIABLE CONTROLLED INFORMATION SYSTEM AND METHODS FOR MONITORING AND ADJUSTING BEHAVIOR

(71) Applicant: Ripple Effects, Inc., Seattle, WA (US)

(72) Inventors: Alice Ray, Alameda, CA (US); Leif Askeland, Greenville, RI (US); Richard J. Maddocks, Barrington, RI (US); Stephen B. Lewis, San Francisco, CA (US); Shelley Smith, Plymouth, MA (US); Eduardo Rodriguez, Tiverton, RI (US); Brian White, Berkeley, CA (US)

(73) Assignee: RIPPLE EFFECTS, INC., Seattle, WA (US)

( * ) Notice: Subject to any disclaimer, the term of this patent is extended or adjusted under 35 U.S.C. 154(b) by 986 days.

(21) Appl. No.: 16/873,792

(22) Filed: Jul. 2, 2020

(65) Prior Publication Data
US 2021/0046392 A1 Feb. 18, 2021

Related U.S. Application Data

(60) Provisional application No. 62/921,835, filed on Jul. 8, 2019.

(51) Int. Cl.
*A63H 3/04* (2006.01)
*A63H 3/00* (2006.01)
(Continued)

(52) U.S. Cl.
CPC .............. *A63H 3/001* (2013.01); *A63H 3/02* (2013.01); *G09B 23/28* (2013.01); *A63H 2200/00* (2013.01)

(58) Field of Classification Search
CPC ......................... A63H 3/001; G09B 23/28–34
See application file for complete search history.

(56) References Cited

U.S. PATENT DOCUMENTS 2,859,731 A * 11/1958 Sutton ................. A01K 15/025
  219/520
3,154,881 A * 11/1964 Elwell .................... A63H 3/001
  434/266
(Continued)

FOREIGN PATENT DOCUMENTS

| WO | WO-2005014133 A1 * | 2/2005 | ............. A63H 29/22 |
| WO | WO-2012141130 A1 * | 10/2012 | ........... A63H 13/005 |
| WO | WO-2018006107 A1 * | 1/2018 | ........... A61H 13/005 |

*Primary Examiner* — Eugene L Kim
*Assistant Examiner* — Matthew B Stanczak
(74) *Attorney, Agent, or Firm* — Hamilton, Brook, Smith & Reynolds, P.C.

(57) ABSTRACT

The disclosed embodiments provide an apparatus and methods for assisting individuals in controlling respiratory rates. For example, a respiratory regulation apparatus is provided in the form of a plush animal toy that operates components to simulate the breathing rate of anxious individuals. The apparatus may include actuators that are controlled by a slotted cam that is dynamically rotated at varying speeds in a determined rotational direction. The actuators move inward and outward in relative directions to move a torso of the plush animal toy to simulate breathing. In certain aspects, actuators may expand outward while at the same time another actuator contracts inward to cause the torso to simulate realistic breathing movements. A processor controls the speed of the cam such that the simulated breathing of the animal toy apparatus can be reduced at a controlled rate to assist an individual in reducing their breathing rate to a calmer state.

15 Claims, 13 Drawing Sheets

(51) Int. Cl.
*A63H 3/02* (2006.01)
*G09B 23/28* (2006.01)

(56) References Cited

U.S. PATENT DOCUMENTS

| | | | | | |
|---|---|---|---|---|---|
| 5,393,259 | A | * | 2/1995 | Lee | A63H 13/00 |
| | | | | | 446/298 |
| 6,695,673 | B1 | * | 2/2004 | Stadbauer | A63H 3/24 |
| | | | | | 446/337 |
| 6,939,195 | B1 | * | 9/2005 | Hunt | A63H 3/001 |
| | | | | | 446/295 |
| 2007/0042670 | A1 | * | 2/2007 | Negrin | A63H 3/24 |
| | | | | | 446/180 |
| 2010/0075570 | A1 | * | 3/2010 | Cameron | A63H 13/02 |
| | | | | | 446/330 |
| 2013/0178982 | A1 | * | 7/2013 | Wong | A63H 3/001 |
| | | | | | 700/258 |
| 2019/0209932 | A1 | * | 7/2019 | Schwartz | H04R 1/028 |
| 2021/0046392 | A1 | * | 2/2021 | Ray | A61B 5/165 |

* cited by examiner

DYNAMIC AND VARIABLE CONTROLLED INFORMATION SYSTEM AND METHODS FOR MONITORING AND ADJUSTING BEHAVIOR

CROSS-REFERENCE TO RELATED APPLICATIONS

This application claims the benefit of U.S. Provisional Application No. 62/921,835, filed Jul. 8, 2019, DYNAMIC AND VARIABLE CONTROLLED INFORMATION SYSTEM AND METHODS FOR MONITORING AND ADJUSTING BEHAVIOR, the specification (including figures) of which is incorporated herein in its entirety.

TECHNICAL FIELD

The following disclosure relates to dynamic and variable feedback systems and, more particularly, to such systems that use electro-mechanical components to provide information to help adjust behavior.

BACKGROUND

Modern society is filled with numerous sources of stress and conflict for most, if not all, people. While many people may have learned or have been exposed to coping mechanisms to manage stress, respiratory rates, anxiety, and unregulated behavior that can result from these conditions, others may not have the maturity, skills, or capability to do so. For example, young children, senior citizens, people with emotional and/or physical challenges, and victims of violence, injury, natural disaster, poverty, or systematic discrimination may be more vulnerable to various forms of traumatic stress. Some may not only lack control of their surroundings and emotions; they may also lack sufficient verbal skills to express their concerns and state of mind. One thing they can learn to control is their breathing, including their awareness of breath, breathing patterns and associated thoughts—which in turn modulate emotion and impact behavior. It is vital to teach people—especially vulnerable young children-ways to use the control they can have over their own breathing, thoughts, and self-talk as a means toward calming themselves, so that they can learn to cope better with stressful situations in order to pursue a healthier emotional, mental, and physical life.

SUMMARY

Methods and systems consistent with the disclosed embodiments provide features that provide dynamic, configurable, and receptive mechanisms aimed to assist users to control and adjust their breathing patterns, thoughts, and self-talk in order to create a stable mental, emotional and physical state. In certain aspects, the disclosed embodiments may have the appearance of a toy, so that a child is likely to interact with the system and receive benefits provided by the processes performed by that system. In other aspects, the disclosed embodiments may have the appearance of a wearable accessory or hardware/software apparatus.

For example, the disclosed embodiments may include an respiratory regulation apparatus that includes a CPU housing including a processor programmed to execute instructions to provide one or more control signals to control one or more components of the apparatus. The apparatus may also include a first actuator that includes a first actuator extension having a first follower and a second actuator that includes a second actuator extension having a second follower. The apparatus may also include an actuator housing that includes a first actuator housing receiving slot that receives the first actuator extension and a second actuator housing receiving slot that receives the second actuator extension. Further, the apparatus may include a slotted cam that connects to a shaft of a motor that is configured to rotate the cam in a first rotational direction, the slotted cam including a continuous oval slot that receives the first follower and the second follower. In certain aspects, the processor may provide one or more of the control signals to control the rotational speed of the motor shaft such that the cam rotates in the first rotational direction at a first rotational speed that causes the first actuator extension to move inward and outward within the first actuator housing receiving slot in a repeating pattern at an actuator movement rate based on the rotational movement of the cam in the first rotational direction and also cause the second actuator extension to move inward and outward within the second actuator housing receiving slot in a repeating pattern at the actuator movement rate based on the rotational movement of the cam in the first rotational direction. Moreover, the processor may dynamically control the rotational speed of the motor shaft such that the cam rotates in the first rotational direction at dynamically decreasing rotational speeds that results in the first and second actuators moving inward and outward within the respective first and second actuator housing receiving slots at dynamically decreasing actuator movement rates.

In other aspects, the apparatus may also include a third actuator having a third actuator extension including a third follower and the actuator housing may include a third slot for receiving the third actuator extension. The cam oval slot may be configured to receive the third follower. In certain embodiments, the actuator housing may also include a first groove that allows the first follower to move in a first linear direction within the actuator housing based on the rotation of the cam in the first rotational direction. The actuator housing may also include a second groove that allows the second follower to move in a second linear direction within the actuator housing based on the rotation of the cam in the first rotational direction. Still further, the actuator housing may include a third groove that allows the third follower to move in a third linear direction within the actuator housing based on the rotation of the cam in the first rotational direction. The respiratory regulation apparatus disclosed above may be configured such that the first linear direction is a direction outward from the actuator housing, the second linear direction is a direction outward from the actuator housing, and the third linear direction is an inward direction toward the actuator housing.

In certain aspects, the respiratory regulation apparatus may be embedded within a plush animal toy that includes a torso that is expanded outward and contracted inward based on movement caused by the first, second, and third actuators in a manner that simulates breathing by the animal toy. The torso may be expanded outward on two opposing sides based on the movements of the first the second actuators by the rotation of the cam in the first rotational direction and, at the same time, the torso may be contracted inward on a different torso side based on the movement of the third actuator by the rotation of the cam in the first rotational direction. The expanded outward and contracted inward torso movement caused by at least the first and second actuators is done in a manner that simulates breathing by the animal toy.

In other embodiments, the respiratory regulation apparatus may also include movable apparatus leg extensions that connect to a body housing that includes the actuators and the cam. In some instance, where the apparatus is embedded within a plush animal toy that includes extremities, the apparatus leg extensions may form part of the animal toy extremities. In certain aspects, at least one of the animal toy extremities resembles a prosthetic leg.

In other aspects, the processor of the respiratory regulation apparatus may generate one or more of the control signals that dynamically control movement of the first, second, and third actuators in a dynamically adjustable pattern that simulates breathing. Where the apparatus is embedded within a plush animal toy, the processor may generate one or more of the control signals that dynamically control movement of the first, second, and third actuators in a dynamically adjustable pattern that simulates breathing of the toy animal.

In other embodiments, the processor of the respiratory regulation apparatus may receive input signals reflecting a breathing pattern of an individual proximate to the apparatus and generates a control signal to control the motor to cause the cam to rotate at a first speed in the first rotational direction such that the first actuator extension moves inward and outward within the first actuator housing receiving slot at a first repeating pattern rate based on the rotational movement of the cam in the first rotational direction. Moreover, the processor may also generate a control signal to control the motor to cause the cam to rotate at a first speed in the first rotational direction such that the second actuator extension moves inward and outward within the second actuator housing receiving slot at the first repeating pattern rate based on the rotational movement of the cam in the first rotational direction. In other embodiments, the processor may generate subsequent control signals to control the motor to cause the cam to rotate at a dynamically decreasing speed in the first rotational direction such that the first actuator extension moves inward and outward within the first actuator housing receiving slot at a corresponding dynamic decreasing pattern rate based on the rotational movement of the cam in the first rotational direction. Further, the processor may generate subsequent control signals to control the motor to cause the cam to rotate at a dynamically decreasing speed in the first rotational direction such that the second actuator extension moves inward and outward within the second actuator housing receiving slot at the corresponding dynamic decreasing pattern rate based on the rotational movement of the cam in the first rotational direction.

In other aspects, the respiratory regulation apparatus may include an audio component for providing audio instructions through a speaker that reflect instructions regarding how to reduce a breathing rate to a calm level and a lighting component that provides repeated lighting at a first lighting rate that is dynamically reduced based on a dynamic decrease in the rotational speed of the cam.

The disclosed embodiments also include a method for providing respiratory regulation assistance through an respiratory regulation toy apparatus including a processor that provides control signals to control the rotational speed of a cam that connects to actuators that each repeatedly move in a respective outward and inward direction and rate relative to the apparatus based on a first rotational direction of the cam. In certain aspects, the method may include receiving, by the processor, a signal reflecting a breathing rate of an individual proximate to the respiratory regulation toy apparatus and controlling, by the processor, movement of the actuators to simulate the breathing rate by the respiratory regulation toy apparatus. The method may further include dynamically reducing the rate of the inward and outward directional movement of the actuators to simulate a dynamic and controlled reduction in the breathing rate of the respiratory regulation toy apparatus. The respiratory regulation toy apparatus may operate to help the individual reduce the individual's breathing rate by providing dynamically controlled physical movements of a torso of the respiratory regulation toy apparatus, the physical movements caused by the dynamic movements of the actuators controlled by the cam rotating in the first rotational direction in such a manner that simulates a breathing pattern of the respiratory regulation toy apparatus.

In other embodiments, the actuators involved in the method may include at least a first actuator and a second actuator and the cam includes a continuous oval slot that receives followers associated with the first and second actuators such that movement of the first and second actuators are controlled by rotational movement of the oval slot in the cam. The method may further include moving the first actuator in a linear direction relative to the torso of the respiratory regulation toy apparatus based on movement of the cam in the first rotational direction, and at the same time, moving the second actuator moves in an linear direction opposite to the first actuator linear direction relative to the torso based on the movement of the cam in the first rotational direction. Moreover, the method may also include providing audio guidance through an audio component of the respiratory regulation toy apparatus to guide the individual to reduce the individual's breathing rate, wherein the audio guidance is synchronized with the dynamic reduction of the simulated breathing rate of the respiratory regulation toy apparatus caused by the dynamically controlled inward and outward directional movement of the actuators.

Additionally, the method may include receiving, by the processor, a signal reflecting a selection of a language for the audio component to provide the audio guidance and providing the audio guidance in the selected language. Moreover, the method may further include receiving, by the processor, a signal reflecting an updated breathing rate of the individual and controlling, by the processor, movement of the actuators to simulate the updated breathing rate by the respiratory regulation toy apparatus.

The above exemplary aspects of the disclosed embodiments are not limiting. Other aspects of the disclosed embodiments may provide other features, such as location monitoring, physical and emotional state monitoring, and associated feedback control, and may include coaching in cognitive-behavioral and social-emotional skill building. These and other exemplary aspects of the disclosed embodiments are described in detail below.

BRIEF DESCRIPTION OF THE DRAWINGS

It is to be understood that both the general and detailed descriptions below are exemplary and are not restrictive of the implementations and aspects of the disclosed embodiments.

The accompanying drawings illustrate exemplary aspects of the disclosed implementations and, together with the descriptions below, provide explanations relating to the general and/or technical features relating to the disclosed embodiments.

DETAILED DESCRIPTION

The following detailed description of exemplary embodiments refers to the accompanying drawings. The same reference numbers in different drawings may identify the same or similar components, functionalities, processes, elements, and the like.

Figure 1:
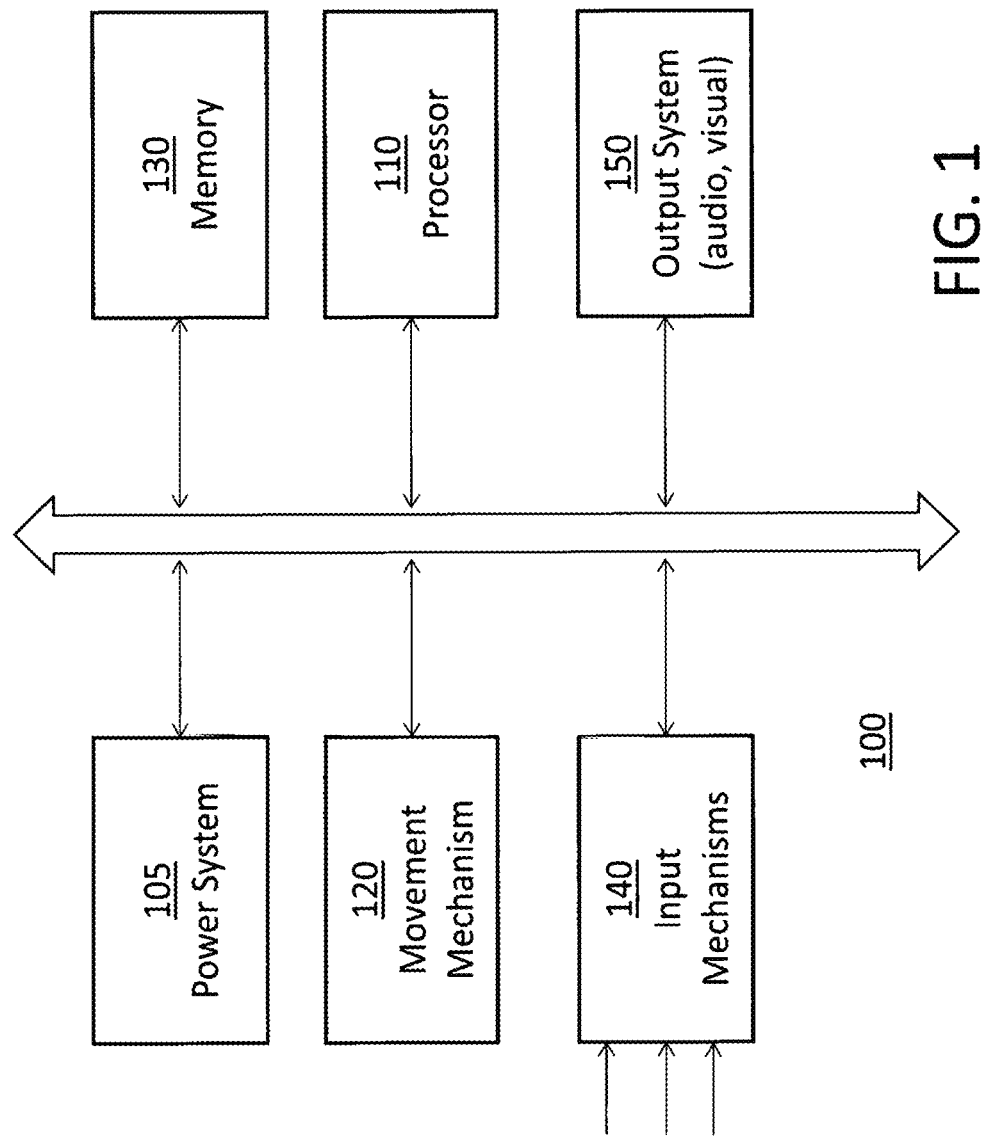
FIG. 1 is a block diagram of an exemplary system consistent with certain aspects of the disclosed embodiments.

Various embodiments of the present disclosure provide a system and process that may be used to guide the cognitive, emotional, social, and/or physical development and self-regulation of a person, e.g., a child or adolescent. FIG. 1 is a block diagram of an exemplary system consistent with certain aspects of the disclosed embodiments. As shown in FIG. 1, a system 100 may include various components that perform one or more aspects of the disclosed embodiments. For example, system 100 may include a power system 105, one or more processor(s) 110, a movement mechanism 120, one or more memories (memory 130), input mechanisms 140, and output system 150. The configuration and arrangement of the components in system 100 may vary. For example, system 100 may further include one or more other components (not shown) that receive and/or provide information for use by other components of system 100 (e.g., processor 110, memory 130, movement mechanism 120, etc.). In certain aspects of the disclosed embodiments, a component may refer to hardware, firmware, and/or software, or a combination thereof. Moreover, certain aspects of the components of system 100 may be combined into a single component to perform functions and processes consistent with the disclosed embodiments. For example, processor 110 may include a memory device that stores information that may be used by processor 110 alone, or in combination with information from memory 130, to perform one or more aspects of the disclosed embodiments.

Power system 105 may include one or more components that provide power to one or more components of system 100. For example, power system 105 may include one or more DC power source(s), such as battery source(s) that provide power to electrical components of system 100. Power system 105 may also include other components, such as power boost circuitry, and related control circuitry for controlling the power to system 100. Additional aspects of power system 105 are described below.

Processor 110 may be one or more processing devices (e.g., microcomputer, microcontroller, and/or CPU(s)) that are configured to execute software instructions stored on one or more memory devices (e.g., memory 130, internal to processor 110, etc.) to perform one or more processes consistent with aspects of the disclosed embodiments. In one example, processor 110 may perform processes that provide information to movement mechanism 120 to control the operation of mechanism 120 to actuate mechanical components of system 100 to cause system 100 to simulate breathing in accordance with certain aspects of the present invention. In another example, processor 110 may perform processes that provide information to output system 150 to produce output (e.g., audible sounds, visible displays, light signals, etc.) in accordance with certain aspects of the present invention. In other aspects, processor 110 may receive information from input mechanisms 140, which upon processing and analysis, provide information to dynamically adjust the operation of movement mechanism 120 and/or output system 150. In still other examples, processor 110 may perform processes that provide information for communication to a remote system for monitoring, feedback control, and other features consistent with the disclosed embodiments. The above examples, and those discussed below, do not limit the disclosed embodiments, as additional features consistent with the operation, functionalities, and processes may be implemented and performed by the disclosed embodiments.

Movement mechanism 120 may be a system that provides mechanical movement relating to system 100 in accordance with certain aspects of the disclosed embodiments. For example, movement mechanism 120 may include one or more actuator(s) for moving one or more mechanical parts of movement mechanism 120 and system 100. Movement mechanism 120 may include one or more motors that drive mechanical components of system 100 to perform one or more aspects of the disclosed embodiments. For example, the motor(s) may be coupled to a gear assembly and/or cam(s) for driving one or more actuator(s), as described further below with respect to exemplary configurations of certain embodiments. Additional features of movement mechanism 120 are described below and are not limited to the above examples.

Memory 130 may include one or more storage devices that store instructions that may be used by processor(s) 100 to perform functions related to the disclosed embodiments. For example, memory 130 may store and provide software instructions that may perform one or more processes when executed by processor 110. In certain aspects, memory 130 may include a single program that, when executed by processor 110, performs certain functions of system 100, or memory 130 may include multiple programs that individually or collectively perform functions consistent with the disclosed embodiments. Memory 130 may also store data that may reflect any type of information in one or more formats that system 100 may use to perform features consistent with the disclosed embodiments. For example, such data may include data files containing information in different languages that may be output by output system 150. Such data may also include data files that are used by processor 110 to display information via output system 150.

Other aspects of memory 130 are described below consistent with the disclosed embodiments. Although FIG. 1 shows memory 130 as a single component, aspects of the disclosed embodiments are not limited to such a configuration. System 100 may include one or more memories 130 that may store data and/or software consistent with certain aspects of the disclosed embodiments. For example, memory 130 may include an audio storage unit and an audio player that maintains and processes audio files for output by output system 150 based on signals provided by processor 110.

Input mechanisms 140 may include one or more devices and related software configured to allow information to be received by system 100. For example, input mechanisms 140 may include one or more user input selection switches (e.g., buttons, selectors, etc.) that enable a user to select one or more different modes of operation consistent with the features provided by system 100. For instance, input mechanisms 140 may include a breathing rate mode selector that enables a user to select one or more breathing modes that are performed by certain applications of system 100. Further, input mechanisms 140 may include one or more song mode selectors that enable a user to select one or more song modes for system 100 to play via audible components of output system 150. Further, input mechanisms 140 may include one or more coaching selectors that enable a user to select delivery of one or more coaching scripts for system 100 to play via audible components of output system 150. Input mechanisms 140 may also include a power control selector that may turn on and off system 100. Input mechanisms 140 may also include a language, voice and dialect selector that enables a user to select a preferred language and voice delivery mode, including mechanical voice delivery of the songs and narration/coaching modes. In some embodiments, system 100 may be configured to perform processes to detect one or more languages. For example, system 100 may include software and associated components that when executed may automatically receive, analyze, and determine the language of a user's speech, and provide signals to components of system 100 to enable the system to automatically adjust output to be compatible with the detected language. Thus, for instance, when a user speaks in a language that may be included in a language library of system 100, the system may detect the language of such speech input and automatically convert to using (e.g., outputting) language files compatible with the detected language. Such processes may enable operation and use of system 100 without requiring a user to manually select the language that will be used for audio output. In some embodiments sound levels and language choices are selectable from a smartphone or other device, and additional songs and coaching to promote self-regulation can be loaded from the phone into the toy apparatus. Input mechanisms 140 may also include a selector that may enable a user to manually enable a heartbeat display mechanism provided in connection with output system 150, matched to the user's respiratory rate or separate from it.

In accordance with certain aspects of the disclosed embodiments, the implementations, features, operations, and functionality of system 100 may be configured for use by children, adolescents, and/or socially vulnerable individuals (e.g., people with developmental impairments, people who have a spectrum of social, emotional and/or behavioral challenges, and people who have experienced traumatic stress, including poverty and systematic discrimination), who may be reluctant to communicate verbally with another human during stressful situations, or whose cultural traditions stigmatize or prohibit such verbal expressions. Therefore, in some embodiments, system 100 may be implemented in the form of a device (e.g., toy apparatus) with which a child or other user may interact. For example, in some embodiments system 100 may be implemented in a plush toy that is equipped with components and functionality designed to help the user calm himself/herself through feedback provided by system 100 via the toy (e.g., through guided breathing, audio and visual stimulus and/or feedback to control breathing, heart rate, self-talk related to behavioral control, etc.).

For example, in certain aspects, system 100 may perform processes that control mechanical components of the toy apparatus to simulate one or more breathing cycles via motorized embodiments of components that simulate the expansion and contraction of a chest cavity of a toy animal (e.g., a plush dog or other animal), along with visual, audible, and/or tactile cues for the user to observe and experience during use of system 100. In this manner, the toy apparatus, via system 100, may provide physical and electronic information that may assist the user to attain increased calmness through guided breathing and/or heart rate control, as the user is encouraged to touch the apparatus and adapt his/her own breathing to synchronize with the breathing patterns demonstrated by system 100. Such guided breathing is valuable particularly for young children, who may not know how to calm themselves after becoming upset. For convenience, system 100 may be referred to as a calming apparatus. Due to the form factor of a toy, the user may be inclined to interact with the calming apparatus and thereby learn from its demonstrated actions and/or behaviors even if the user is a young child or a person whose exposure to traumatic stress has made it difficult for him/her to learning through written or verbal communication.

One embodiment in the form of a toy animal includes a prosthesis (e.g., as shown in FIGS. 3A-3E) or similar physical manifestation of the emotional vulnerability a user may feel. Such an embodiment is particularly well suited for calming young children.

Other form factors, including but not limited to wearable accessories, hardware/software apparatus, electronic games, and/or mechanical robots, may be suited for older children and adolescents.

Figure 2:
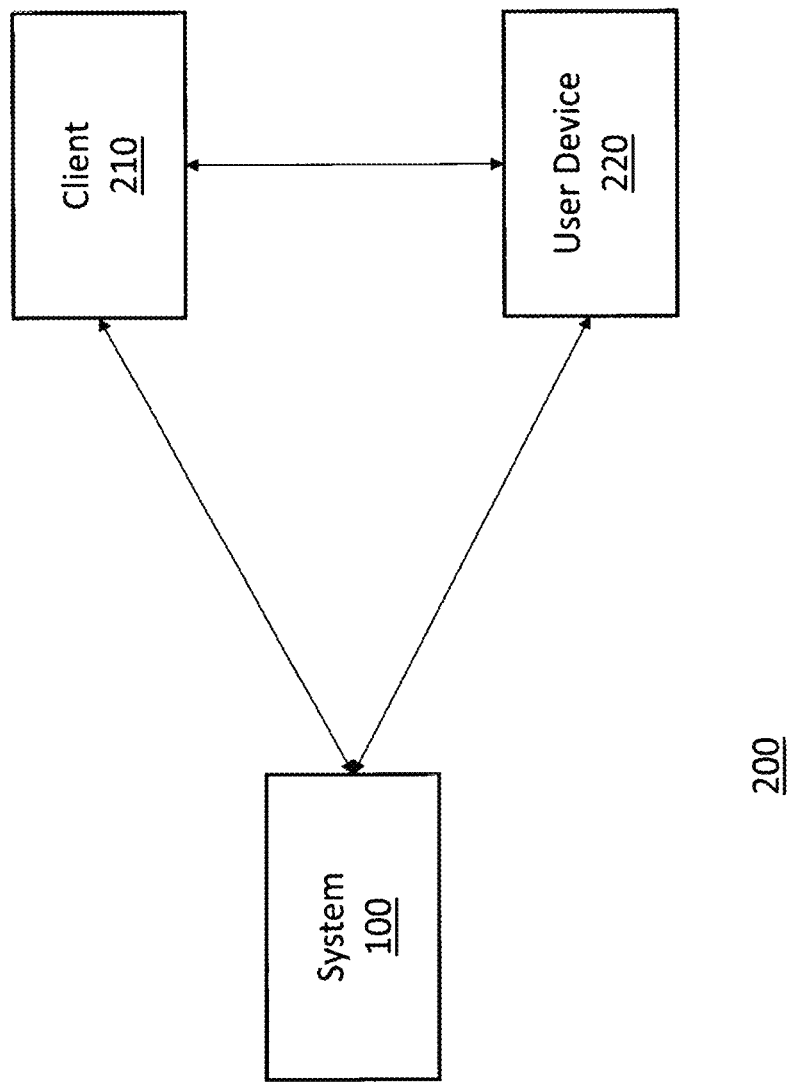
FIG. 2 is a block diagram of another exemplary system, consistent with certain aspects of the disclosed embodiments.

FIG. 2 shows a block diagram of an exemplary system 200 in accordance with certain aspects of the disclosed embodiments. System 200 may include system 100 (consistent with system 100 described for FIG. 1 and below), client 210, and user device 220. In certain aspects, system 100, client 210, and user device 220 may be interconnected via one or more communication links that send and receive information over one or more communication media. For instance, the communication link(s) may be any type of network configured to provide communications between components of system 200. In certain aspects, the network communication link between one or more system 100, client 210, and/or user device 220 may be any type of network (including infrastructure) that provides communications, exchanges information, and/or facilitates the exchange of information, such as the Internet, a Local Area Network, or other suitable connection(s) that enables the sending and receiving of information between the components of system 100, and/or combinations of networks (e.g., public network and private networks). For instance, the network communication link may include wireless communication paths and infrastructures that enable information to be wirelessly exchanged between remote components of system 200. Such wireless communications may include known wireless communication technologies, including NFC, Bluetooth, or other longer-range wireless communication technologies, such as those involving Wi-Fi technologies. The infrastructure associated with such wireless communication link(s) are not shown, but are understood by one of ordinary skill in the art to operate to facilitate wireless communications between one or more of the components of system 200. In such instances, system 100 may be configured with wireless communication input/output components, including circuitry and software that enable system 100 to send and receive information wirelessly via the network communication link(s) in system 200.

In certain aspects, client 210 may be a client device that is remote from system 100 and is operated by a user. In certain embodiments, client 210 may be a mobile device, such as a smartphone, tablet, mobile laptop computer, personal data assistant, robot, or other type of mobile computing device that is configured with features consistent with certain aspects of the disclosed embodiments. For instance, client 210 may include one or more computing devices that execute software instructions stored in memory to perform one or more processes consistent with the disclosed embodiments, such as receiving feedback information from system 100 and sending control information to system 100 via the wireless network communication link(s) of system 200. Similarly, client 210 may include one or more memory device(s) storing data and software instructions and one or more processor(s) programmed and arranged to use the data and execute the software instructions to perform processes consistent with the disclosed embodiments. In certain aspects, client 210 may be a mobile device that stores a mobile application that provides information to a user via a display of client 210 and receives input from a user of client 210 that is processed, transmitted to system 100, for controlling one or more features of system 100 consistent with the disclosed embodiments. Such features may include, but are not limited to, interactive games, music, art activities, and various things derived from them. The mobile application executed by client 210 may also receive alerts from system 100 that are processed by client 210 to provide audible and visual information associated with certain characteristics of a user associated with system 100.

User device 220 may be a computing device that is associated with a user of system 100. In certain examples, user device 220 may be a device that attaches to a user (e.g., a wrist bracelet, wrist watch, necklace, etc.) that interacts with one or more sensors to monitor one or more characteristics of the user of user device 220. In certain aspects, user device 220 operates in connection with the operation of system 100 to provide feedback to client 210 associated with one or more characteristics of the user of user device 220. For example, in certain aspects, user device 220 may be a computing device that attaches to the wrist of a user who interacts with the toy apparatus embodiment of system 100 described above. In certain aspects, user device 220 may connect to one or more sensors that monitor heart rate variability and/or breathing rate of the user, or other characteristics (e.g., body temperature, etc.). User device 220 may be configured to collect the user characteristic data and wirelessly transmit the information to system 100. In response, system 100 may perform one or more user-characteristic analysis processes that assess the information to determine whether a user characteristic event is triggered, and if so, generate an alert message that is wirelessly transmitted to client 210, which may be associated with the user's parent, guardian, or other person with supervisory responsibilities, or to a support person identified by another person or entity. Client 220 may be configured to display alert information in a display that identifies one or more of the user's characteristics (e.g., heart rate, breathing rate, etc.). In response, client 220 may receive input from the user to adjust the operating mode of system 100 such that processor 110 of system 100 associated with the apparatus may perform one or more functions consistent with the disclosed embodiments, including but not limited to context-specific coaching in social-emotional skill training to develop resilience in the face of stress.

Thus, in some embodiments, an individual other than the person interacting with system 100 (e.g., the user's parent, guardian, or other person with supervisory responsibilities, or a support person as discussed above) can use client device 220 (e.g., running a smartphone app) to control operation of system 100 remotely based on detected feedback. Such an individual can receive audio and/or video data (e.g., via a camera or microphone of system 100) in order to hear and see the user, and can control the system 100, e.g., via commands that are transmitted wirelessly from the individual's smartphone to system 100.

In other embodiments, processor 110 may be configured to perform one or more processes that dynamically adjust the operating mode and functionalities of system 100 in response to characteristic data received from user device 220, without waiting for control information to be received from client 210. For instance, processor 110 may be configured to execute software stored in memory 130 that automatically and dynamically adjusts the breathing rate, heart rate, and audible or visual output information, as the user characteristic data changes from user device 220. In this way, system 100 in, for example, the apparatus, may adjust the type of self-help strategies that may be provided to a user interacting with the toy apparatus based on real-time feedback of user characteristic data collected and provided from user device 220.

In some embodiments, the user device 220 that the user wears as discussed above (e.g., a wrist bracelet, wrist watch, necklace, etc.) provides automatic feedback to system 100 to control modes of operation. For example, an audio analysis program running in system 100 processes audio data received from a microphone of system 100 or user device 220, and detects and interprets sounds associated with predetermined conditions such as distress conditions (e.g., the sound of a person crying) or happiness conditions (e.g., the sound of a person laughing). The audio analysis program provides such sounds to system 100, so that when the user device 220 is in the vicinity of the toy apparatus, the toy apparatus can detect the distress condition or happiness condition and react automatically in accordance with the configuration of system 100. For example, system 100 (which can be configured in the form of a toy apparatus or similar vehicle) can automatically perform a spoken query (e.g., "You sound upset. Shall we try to calm down together?"). System 100 may be triggered to begin predetermined coaching operations based on detected movement or the like. For example, system 100 may be configured to detect movement when a user touches and/or picks up system 100 (e.g., which again can be in the form of a toy apparatus). Sensors in system 100 may provide signals to initiate one or more processes consistent with the disclosed embodiments, such as performing a coaching process that assists the user through breathing and stress-reducing practices consistent with disclosed embodiments. In some embodiments, system 100 may monitor user characteristics during the process and detect changes to such characteristics (e.g., breathing rate slows, crying is reduced, etc.). In turn, system 100 may perform processes that enable the system to adjust the rate and breathing cycles of the system (e.g., which can be configured as a toy apparatus) in appropriate fashion, in synchronization with audio cues received via a microphone of system 100.

Figure 5:
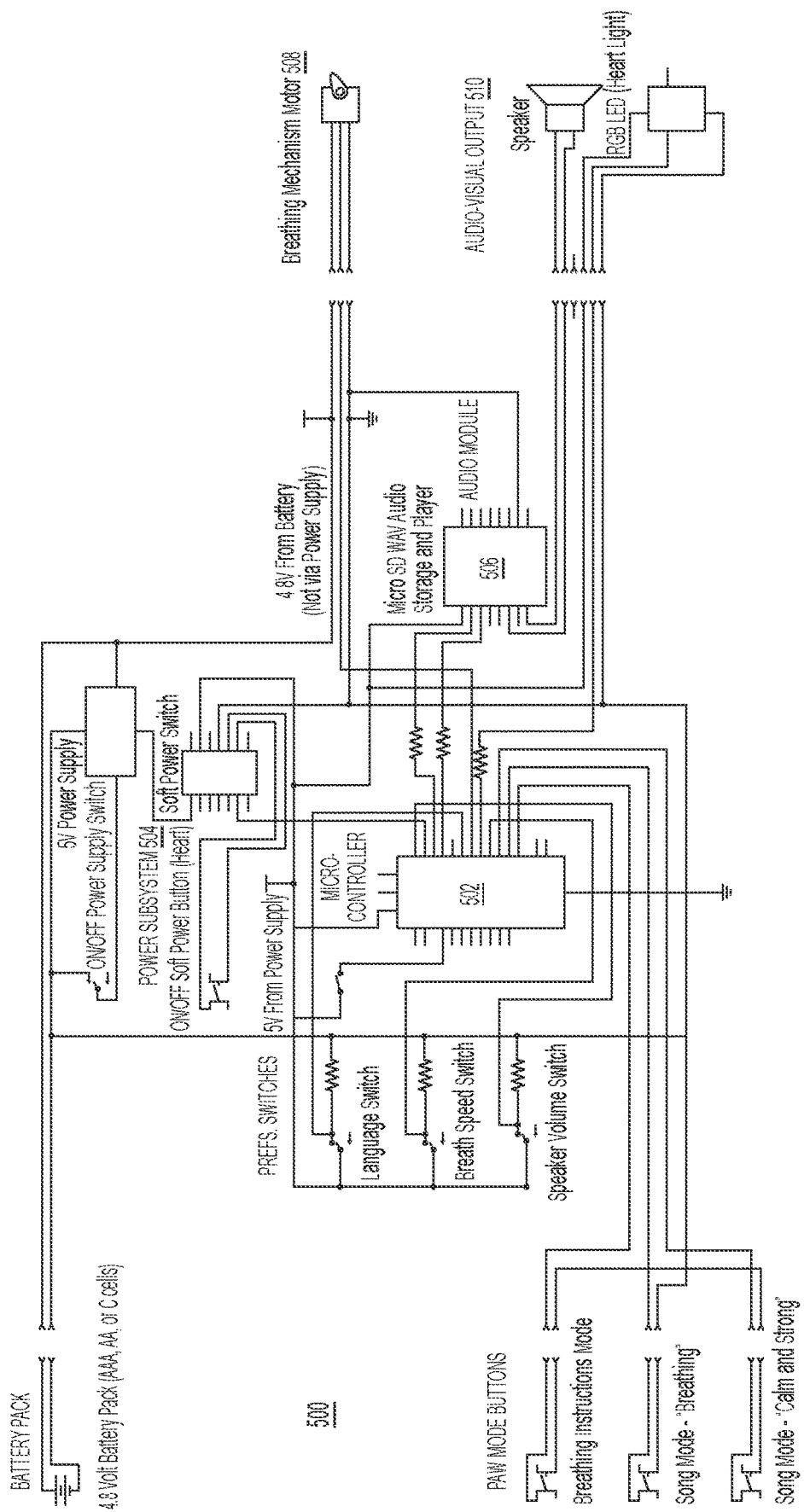
FIG. 5 is a block diagram of an exemplary diagram of system components, consistent with certain aspects of the disclosed embodiments.

FIG. 5 shows a block diagram of an exemplary system 500 that may correspond to system 100. As shown, system 500 may include components that correspond to components of system 100 described above and below. For example, a microcontroller 502 may correspond to processor 110 of system 100, switches and raw mode buttons may correspond to input mechanism 140 of system 100, audio module and audio-visual output may correspond to output system 150 of system 100, battery pack and power subsystem may correspond to power system 105, etc. System 500 is exemplary, and the disclosed embodiments are not limited to the configuration and components as shown in FIG. 5.

Figure 3A:
FIGS. 3A-3E are diagrams of an exemplary apparatus, consistent with certain aspects of the disclosed embodiments.
Figure 3B:
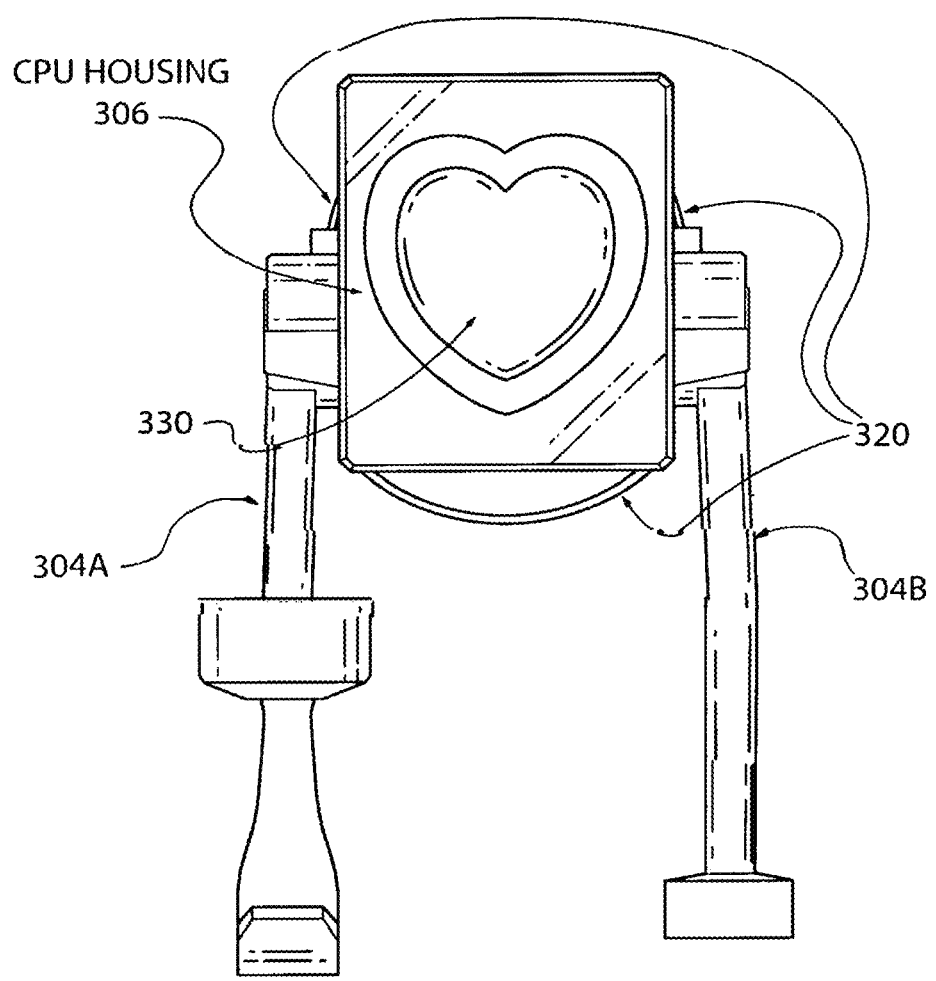
Figure 3C:
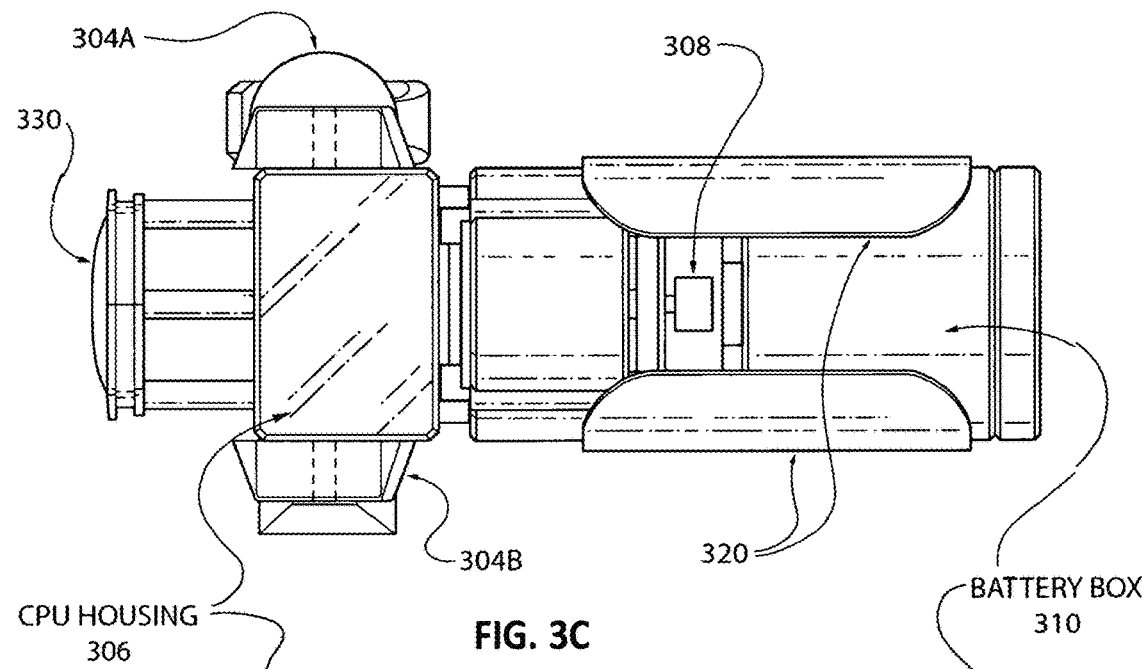
Figure 3D:
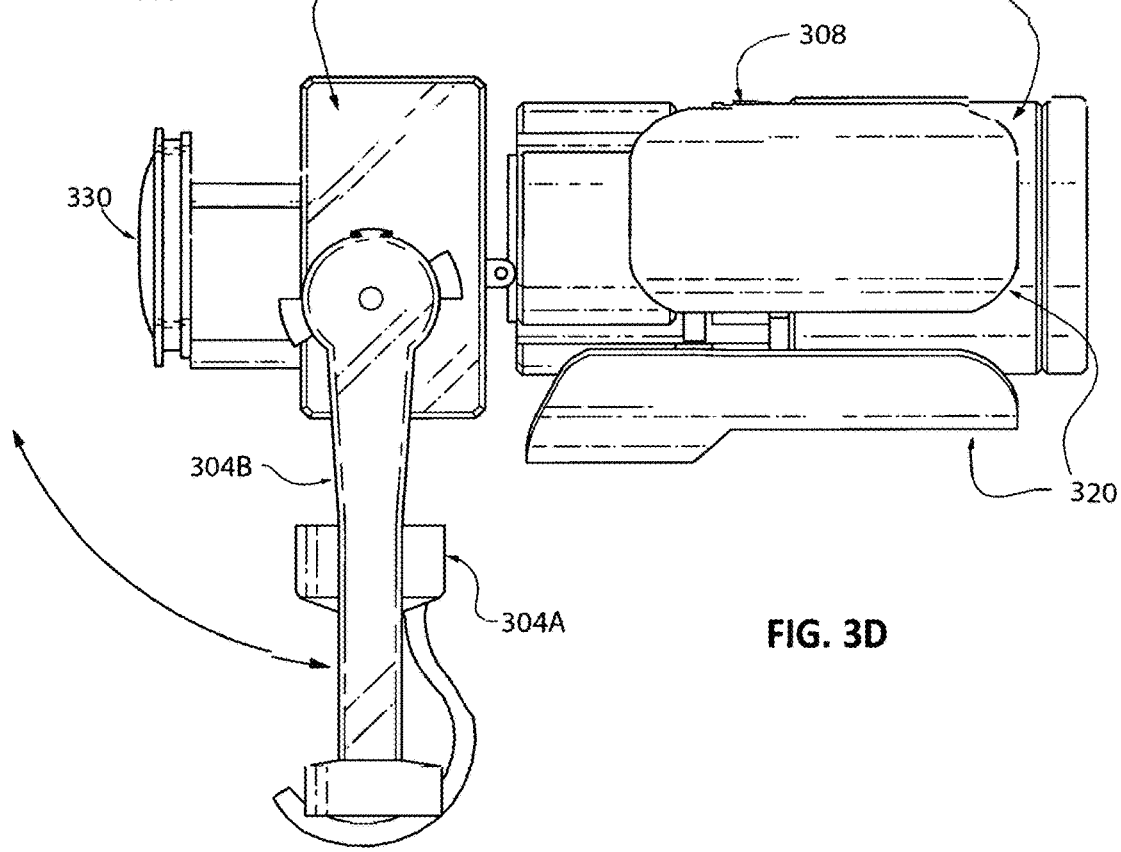
Figure 3E:
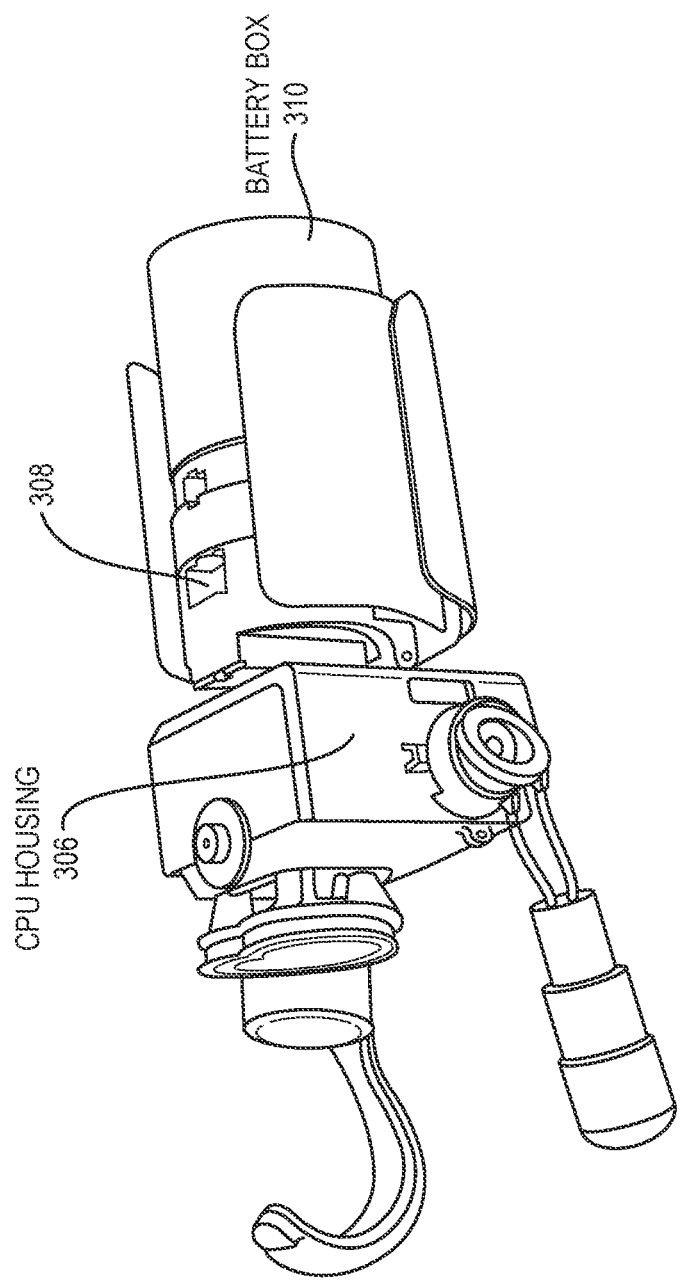

FIG. 3A shows an example of an apparatus 300 in accordance with certain embodiments. The exemplary apparatus 300 may reflect the internal skeleton components of a toy apparatus that may perform features and operate consistent with the features disclosed herein relating to system 100. In one embodiment, apparatus 300 may include a body region that is dimensioned so as to resemble a toy animal, e.g., a dog or cat. For example, FIG. 3A shows apparatus 300 as a toy apparatus (within a plush dog toy). FIGS. 3B-3E show different views of apparatus 300. FIG. 3B shows a front view, FIG. 3C shows a top view, and FIG. 3D shows a side view of apparatus 300. The body region of apparatus 300 may include a CPU housing 306 (e.g., for enclosing components, such as processor 110), a housing 308 (e.g., for enclosing components, such as mechanism(s) for controlling movement mechanism(s) 320, etc.), and a power source housing (battery box 310) for enclosing a power source, such as a battery. Front legs 304A and 304B are extremities (e.g., legs) that may be moved in various ways relative to the body region based on control signals provided by processor 110 and movement mechanism(s) 320, to achieve various positions of the toy apparatus animal. For example, FIG. 3E shows apparatus 300 with front legs 304a and 304b in a different orientation relative to the body region of apparatus 300 than in FIGS. 3A-3D.

In certain embodiments, toy apparatus 300 may be configured to foster increased tolerance and emotional awareness on the part of the user based on the appearance and/or functionality of the apparatus. For example, as shown in FIGS. 3A, 3B, and 3D, front leg 304A may be configured as one or more versions of a detachable prosthetic leg, each version having utility for one or more specific functions, (e.g., running, skiing, swimming) so that toy apparatus 300, as the stand-in for a teacher/coach, demonstrates the potential of people who have undergone adversity to thrive and lead despite those circumstances, and increases awareness, empathy, and respect of the user towards people with prosthetic limbs and other disabilities. Wireless interaction with the related tablet or phone app enables users to extend physical interaction between the animal toy character and the user through games, songs etc.

In certain embodiments, toy apparatus 300 may be configured such that the form factor, including prosthesis, is mirrored on a smartphone or computing device (e.g., via wireless communications), where it is animated so that the user can have a wider physical experience of interactivity with the apparatus.

Figure 6B:
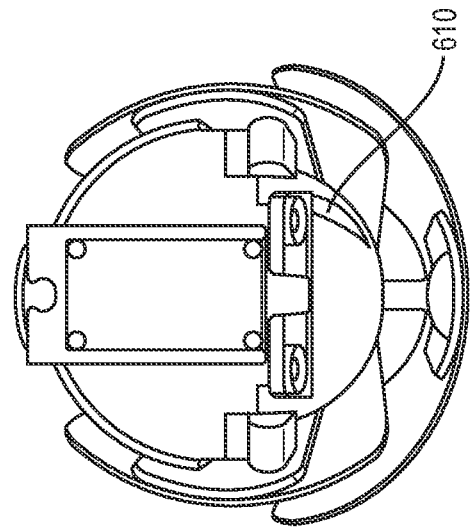
FIG. 6B shows a diagram of an exemplary configuration of actuator components with a slotted cam, consistent with certain aspects of the disclosed embodiments.
Figure 6A:
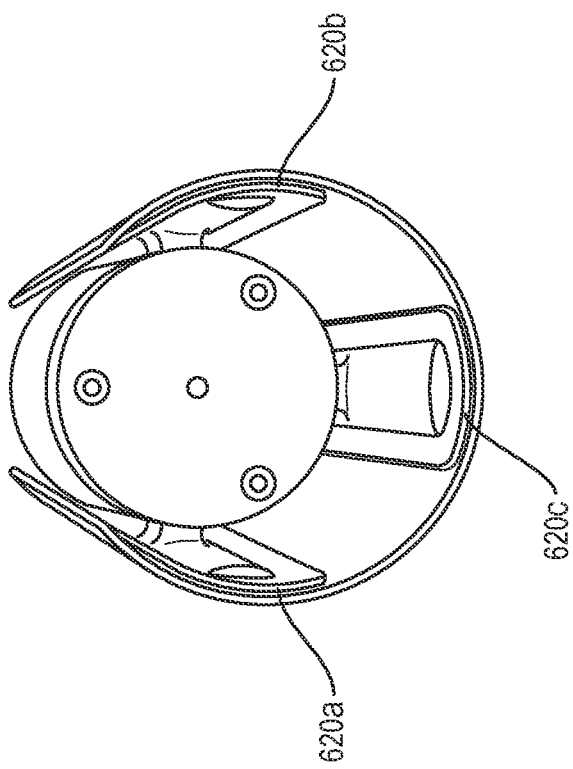
FIG. 6A shows a diagram of an exemplary configuration of actuator components, consistent with certain aspects of the disclosed embodiments.

In some embodiments, toy apparatus 300 includes one or more actuators 320 that may correspond to the movement mechanism 120 described with reference to system 100 of FIG. 1. Actuators 320 may be driven by a motor that is controlled by a microcontroller, such as for example, processor 110, to allow apparatus 300 to perform features like those described above for system 100. For instance, apparatus 300 may be configured, via system 100, to provide motions of the actuator (also described below) to move in a manner that resembles a breathing cycle, e.g., with an inhalation phase and an exhalation phase. In certain aspects, toy apparatus 300 can be enshrouded by an outer skin that may resemble any of various animals (e.g., a dog as shown in FIG. 3A) and that may include a plush fabric, for example. Different outer skins can be used in conjunction with apparatus 300 (or other embodiments of apparatus 300 and system 100). For example, FIGS. 6A and 6B show exemplary embodiments of some internal components that may be implemented with apparatus 300. As described below, in certain aspects, apparatus 300 may be configured, via system 100, to provide motions of the actuator (described further below) that cause the outer skin to move in a manner that resembles a breathing cycle, e.g., with an inhalation phase and an exhalation phase.

Apparatus 300 may also include a lighting unit 330 connected to the body region of the apparatus. In certain embodiments, lighting unit 330 may be associated with output system 150 described above in connection with system 100. For example, apparatus 300 (in connection with system 100) may be configured such that lighting unit 330 displays light output according to various colors and patterns, e.g., via output devices (e.g., one or more light emitting diode (LED) display device circuitry) located within lighting unit 330 and controlled by a microcontroller, such as processor 110. In one example, lighting unit 330 may be configured in the shape of a heart such that during operation, a lighted image of a heart is illuminated in synchronization with the processes performed by processor 110 that may be viewed through the outer skin of apparatus 300. Other shapes and sizes of lighting unit 330 may be implemented with apparatus 300. These and other features are described further below.

Figure 4A:
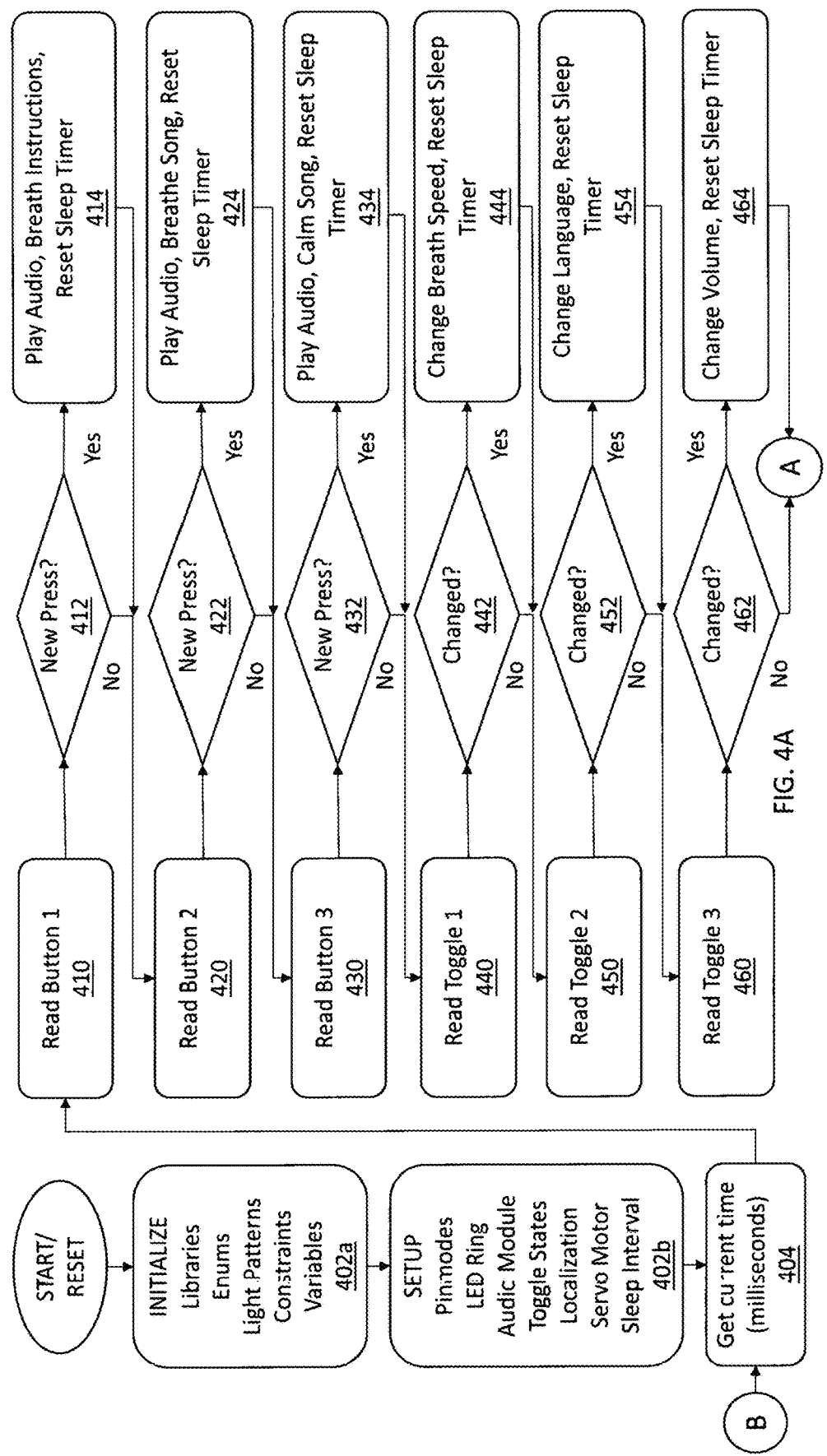
FIGS. 4A-4B collectively show a flow diagram of an exemplary process that may be performed by the disclosed embodiments.
Figure 4B:
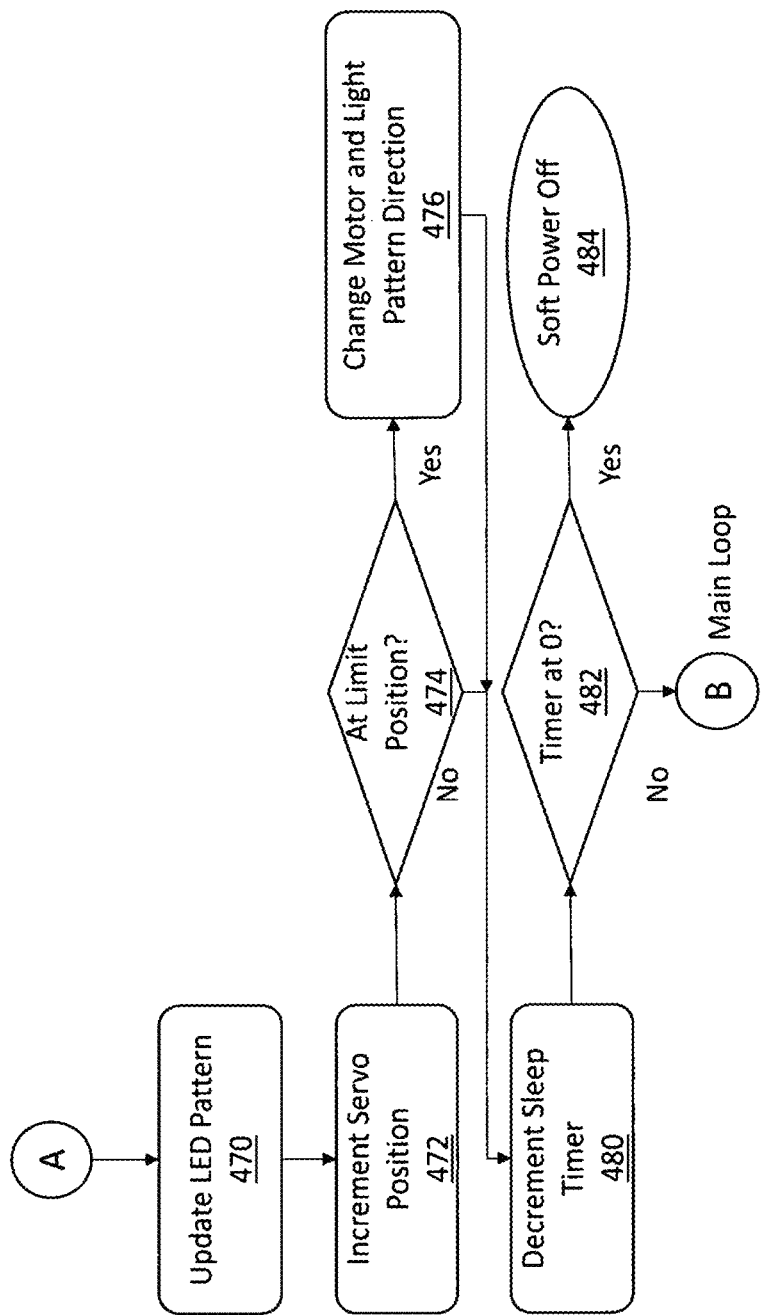

FIGS. 4A-4B collectively show an exemplary flow diagram of a process 400 that may be performed by system 100 (and apparatus 300) in accordance with certain disclosed embodiments. Process 400 may begin upon power-up or reset of system 100 (e.g., via a power button or a reset button). In certain aspects, system 100 may perform initialization 402a and setup 402b process.

Initialization process 402a may include initializing and configuring the following:

Libraries—included libraries allow higher level control of the servo mechanism (servo) motor, micro-controller, software serial ports, audio waveform storage and playback module, paw buttons, and individually addressable LED RGB light ring (pulsing heart light).

Enums (Enumerations)—named values for constants that define various lighting patterns for the LED light ring, and the direction of the patterns.

Light Patterns—Initialize various patterns, directions, and fading effects for the LED light ring.

Constants—Constants that define vibration sensitivity threshold and interval, micro-controller pin for LED light ring, pins for buttons that the user can press, button de-bounce time intervals, sleep timer interval, software serial receiver and transmitter pins, servo motor pin, servo motor angle degree limits, language codes for localization (English, Spanish, etc.), number of lights in LED light ring.

Variables—Variables define the actual hardware buttons, store the toggle state of the toggle switches, the current state of localization (language selected), the software serial interface, audio volume, audio storage folder for localization, servo position, servo interval, servo increment, LED light interval, breath direction, current time, sleep timer, previous sleep time, vibration timer, last time button pressed, last time servo moved, last time LED light changed, LED light index, vibration sensor analog reading Setup process 402b may be performed after each hardware reset. It includes pin modes to set previously defined pins as output pins, set LED pin to OFF. It may also include setting the specific color, pattern, and direction of an LED ring used in apparatus 300, including an LED display that may be presented via LED 330 (LED Ring). Setup process 402b may also including configuring the audio player volume and equalization (e.g., bass and treble control settings) (Audio Module) and configuring initial control parameters for the servo motor (Servo Motor) and the sleep interval for apparatus 300 (Sleep Interval) that controls when to automatically turn off system 100 in apparatus 300.

In certain aspects, processor 110 may perform processes that obtain a current time, e.g., in milliseconds (although other time frames are contemplated by the disclosed embodiments) (block 404). In certain aspects, processor 110 may perform functions that analyze the current time to turn off system 100 (and toy apparatus 300) based on a sleep timer, for example.

In accordance with certain aspects, system 100 may perform processes that detect one or more events, which may be initiated automatically or based on an input provided by an input device (e.g., via input mechanisms 140). For example, system 100 (and toy apparatus 300) may include one or more buttons and/or switches that may be selected by a user. Such buttons and/or switches may be physical (e.g., mechanical and tactile in nature), or they may be virtual buttons and/or switches displayed on a display device (e.g., touch screen display, such as a liquid crystal display (LCD), light emitting diode (LED) display, or any other kind of display or monitor known to those of ordinary skill in the art. Processor 110 may be configured to perform processes that provide information that is displayed in such a display device that may be provided in system 100 (and toy apparatus). In other embodiments, the inputs may be provided in a remote device, such as client 210 or user device 220. In response to input provided, for example, in client 210, system 100 may perform processes that detect an event corresponding to such received input (via, for example, input mechanisms 140). For exemplary purposes only, process 400 shows processes corresponding to three buttons (e.g., Button 1 to Button 3) and three toggle switches (e.g., Toggle 1 to Toggle 3) which may reflect input received via input mechanisms 140 of system 100 (e.g., shown via blocks 410, 420, 430, 440, 450, 460). For instance, buttons 1 to 3 may correspond to exemplary buttons shown in FIG. 5, and toggle 1 to toggle 3 may correspond to toggle switches (e.g., language switch, breath speed switch, speaker volume switch) shown in FIG. 5.

System 100 may perform processes that read Button 1 (block 410) to detect a button press (block 412), and if detected (block 412, Yes), system 100 may perform processes (block 414), e.g., play audio message, such as audible instructions to the user as to how to breathe, (e.g., "Put one hand on my belly and one hand on yours, and let's breathe together. Breathe in, and breath out."), and simultaneously perform processes via the components of system 100 to demonstrate via toy apparatus 300 suggested breathing cycles for the user to follow, etc. System 100 may also reset the sleep timer for operations of system 100. In some embodiments, the sleep timer is a component of the software that runs on the micro-controller (block 502) and that includes an automatic countdown (in, seconds, for example) set from 600 to 0 (providing a duration of 600/60=10 minutes). When the timer reaches 0, the apparatus automatically goes into low power "sleep" mode, as if the user had pressed the power button to turn the apparatus off. Anytime the user interacts with the apparatus, such as when pressing one of the foot buttons or toggling one of the switches, the timer is reset back to a predetermined value, e.g., 600. This ensures that as long as the user is actively using the apparatus, the timer will never reach 0. But if the user is finished interacting with the apparatus (perhaps because the user falls asleep, or simply forgets to it off when finished), it will go into the low power sleep mode after 10 minutes of inactivity. This interval can be easily changed in software.

System 100 may also perform processes that read Button 2 at block 420, and if a button press is detected (block 422), audio output may be played (block 424), e.g., a song that guides the user through a suggested manner of breathing (e.g., a breathing song). System 100 may also reset the sleep timer for operations of system 100.

System 100 may also perform a process that reads Button 3 at block 430, and if a button press is detected (block 432), audio may be played (block 434), e.g., a calming song that may be any song that is intended to have a soothing effect on the user. System 100 may also reset the sleep timer for operations of system 100.

System 100 may also perform a process that reads toggle switch 1 at block 440, and if a state change is detected (block 442), a breath speed for the operation of components of system 100 may be altered (block 444). For example, the breath speed may control the rate at which the breathing song is played, and it may control the rate at which the outer skin of the calming apparatus mechanically contracts and expands (based on motor and actuators in system 100 (e.g., apparatus 300)) to simulate breathing, as discussed below. System 100 may also reset the sleep timer for operations of system 100.

System 100 may also perform a process that reads toggle switch 2 at block 450, and if a state change is detected (block 452), system 100 may change the language used for outputting audio via output system 150 (block 454). System 100 may also reset the sleep timer for operations of system 100.

System 100 may also perform a process that reads toggle switch 3 at block 460, and if a state change is detected (block 462), system 100 may change the volume used for outputting audio (block 464). System 100 may also reset the sleep timer for operations of system 100.

In accordance with certain embodiments, exemplary buttons 1-3 and toggle switches 1-3 may be implemented in various ways. For example, the toggle switches can be implemented as binary switches, or they may each have more than two states that can be progressed in cyclical fashion.

At block 470, system 100 may perform a process to update a lighting pattern, which may cause a lighting assembly to become illuminated in a corresponding manner. For example, in certain aspects, system 100 may perform processes that may change a light display via lighting mechanism 330 as described above for FIG. 3A of toy apparatus 300.

At block 472, system 100 may perform processes that may increment a servomechanism (servo) position corresponding to components of system 100 that facilitate movements of toy apparatus 300 in accordance with disclosed embodiments. For example, in one embodiment of system 100 (and toy apparatus 300), processor 110 may perform processes that control the operation of a motor in one or more modes. For instance, processor 110 may perform processes that operate a motor in two modes that cause rotation of a cam in a first direction or a second direction. Such movements may correspond to movement of mechanical parts of system 100 that simulate the breathing of toy apparatus 300 in accordance with certain embodiments. For example, system 100 may determine whether the servo is at a limit position as detected by the processor 110 (block 474), and if so (Yes), the motor direction may be changed (block 476). The limit position may be analogized to the end of an inhalation phase of the breathing cycle (or the end of an exhalation phase), for example. System 100 may also perform processes that change the light pattern at block 476, e.g., to cause lighting assembly 330 to be illuminated in different cycles of light, different colors, combinations of such features, etc. For instance, processor 110 may perform processes so that based on the detection of the cam at a first limit position (e.g., block 474, Yes), signal(s) may be provided to output system 150 components that causes lighting assembly 330 to change colors of display, such that during operation, lighting assembly 330 may display light in a first color during the inhalation phase of a simulated breathing cycle and in a second color during an exhalation phase.

At block 480, system 100 may perform processes that decrement the sleep timer. System 100 may determine whether the timer is at a predetermined limit (block 482), and if so system 100 may perform processes to perform a "soft power off" process (e.g., as described above, power to certain components of system 100 (apparatus 300) may be powered down without a user having to manually engage a power switch or button) (block 484). If system 100 determines that the timer is not at the predetermined limit (block 482, No), process 400 may return to block 404 (shown as "Main Loop" in FIG. 4B). In this exemplary process, system 100 (and apparatus 300) may continuously check for button events or toggle switch events and may disable the power to one or more components of system 100 if no events have been detected for a predetermined period of time associated with the sleep interval information configured during "Setup" process 402b.

FIG. 5 is a block diagram of an exemplary schematic diagram of system 500 that may correspond to system 100 (and apparatus 300) in accordance with certain embodiments. Components of system 500 may correspond to components of system 100 (and apparatus 300) as described herein. For example, system 500 may include a microcontroller 502 that may correspond to processor 110 described above with reference to FIG. 1, and performs processes for controlling functions and components related to system 500. Microcontroller 502 and the other components in FIG. 5 may be implemented in various ways. For example, while a pinout corresponding to an exemplary Arduino Nano microcontroller is depicted in FIG. 5, other pinouts, processor devices, etc. can be implemented for system 500. System 500 may also include a power subsystem 504 that includes components for controlling power for system 500 from one or more power sources, e.g., a switching power supply, a battery etc. System 500 may also include buttons (e.g., Raw Mode buttons) for a breathing instructions mode, breathing song mode, and calming song mode as shown in FIG. 5. These buttons may correspond to the operations described above in connection with blocks 414, 424, and 434 of FIG. 4. System 500 may also include switches ("Prefs. Switches") for changing language, changing breath speed, and changing speaker volume as shown FIG. 5, which may in certain aspects, correspond to the operations described above in connection with blocks 444, 454, and 464 of FIG. 4A. Exemplary system 500 may also include an audio module 506, a motor 508, and an audio-visual (AV) output module 510, which may include a speaker and a lighting unit, that perform operations consistent with the features of the disclosed embodiments of system 100 (and apparatus 300). In some embodiments, apparatus 300 includes a headphone connection jack, to enable the user to hear audio discreetly via wired headphones, which may be desirable to avoid attracting undesirable attention to the user during a stressful situation. Wireless audio interfaces and corresponding components (hardware and software) may be implemented to provide wireless headphone functionalities (e.g., Bluetooth™ headphone capabilities, etc.). The disclosed embodiments may also be configured with wireless headphone software and components known to those skilled in the art to enable use of wireless headphone audio functionalities.

System 500 may include additional components and features not shown in FIG. 5. For example, system 500 may include microphone circuitry and corresponding software that may permit the user to provide voice input, and capacitive sensors to enable system 500 to detect touch input from the user. System 500 may also include audio watermarking, e.g., by embedding a unique identifier into the audio signals represented in audio files, wherein the identifier travels with the audio files and imprints ownership to help detect unauthorized distribution and/or usage of content. In other aspects consistent with the features described above in connection with system 100 and system 200, system 500 may also include circuitry and components for communicating wirelessly with a remote device, e.g., via communication protocols or techniques such as Bluetooth™, Wi-Fi, and/or infrared communication. In some embodiments, such devices may extend, enhance, and/or provide additional interactivity with the toy apparatus, e.g., through the attached prosthetic or other mechanisms.

Figure 7:
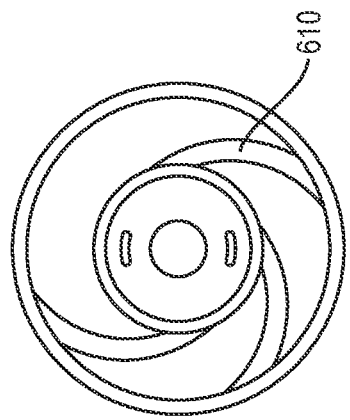
FIG. 7 shows a diagram of an exemplary slotted cam that is rotatable by a motor, consistent with certain aspects of the disclosed embodiments.

FIGS. 6A, 6B, and 7 show diagrams of exemplary components for providing breathing cycle functionalities for system 100 (and system 500 and apparatus 300). For example, FIG. 6A shows exemplary components that may be included in apparatus 300, such as actuators 620a, 620b, and 620c that may be configured to operate in accordance with processes performed by components of system 100 (and system 500 and apparatus 300). The disclosed embodiments are not limited to the exemplary actuators shown in FIG. 6A, as additional or fewer actuators of different configurations may be implemented consistent with the features of the disclosed embodiments. As shown in FIG. 6A, exemplary actuators 620a-620c may have a curved shape for contacting an outer skin (not shown in FIG. 6A) that will surround the housing for the actuators and system 100 (and system 500 and apparatus 300), although different shapes may be used consistent with the disclosed embodiments.

FIG. 6B shows the opposite end of the components shown in FIG. 6A, which includes an exemplary slotted cam 610 that interfaces with the actuators 620a-620c. FIG. 7 shows a diagram of an exemplary slotted cam 610 that may be included in system 100 (and used with system 500 and apparatus 300). In certain embodiments, system 100 (and system 500, and apparatus 300) may perform processes that control actuators 620a-620c) and the slotted cam 610 to provide mechanical movements consistent with the disclosed embodiments (e.g., provides breathing cycle movements).

Figure 8B:
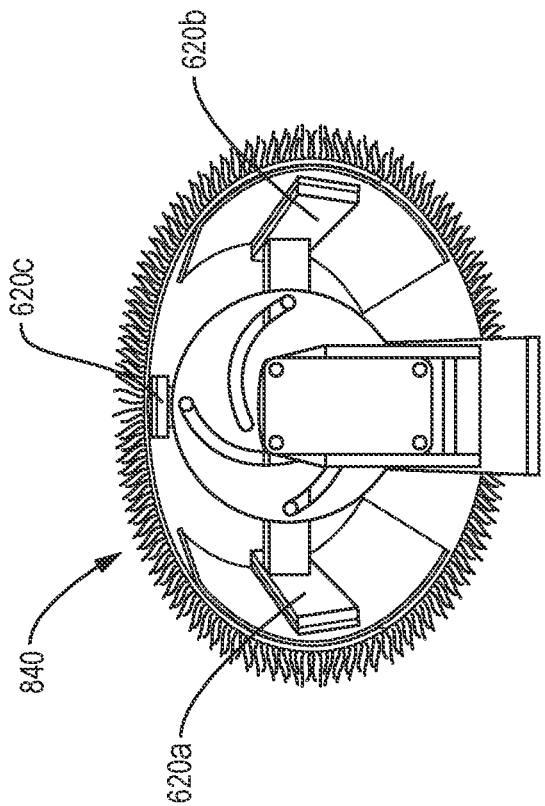
FIG. 8B shows another diagram of an exemplary configuration of actuator components with the slotted cam of FIG. 7, consistent with certain aspects of the disclosed embodiments.
Figure 8A:
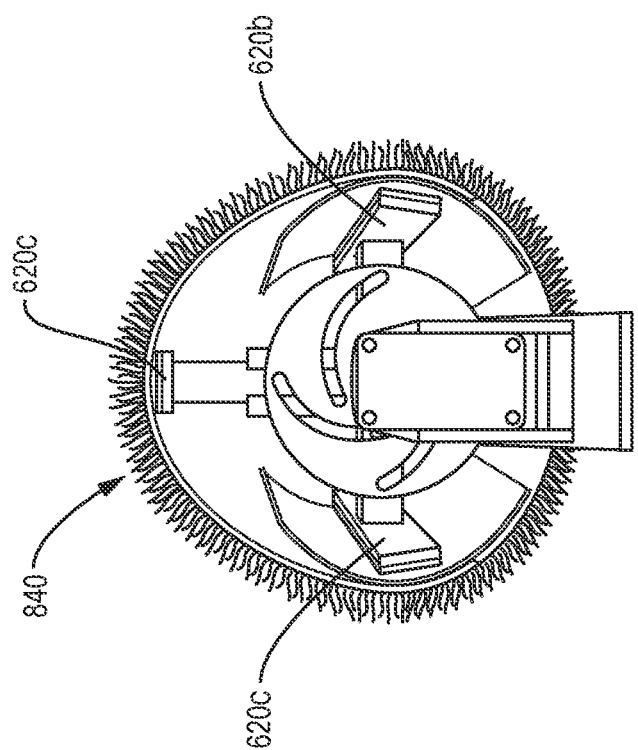
FIG. 8A shows a diagram of an exemplary configuration of actuator components with the slotted cam of FIG. 7, consistent with certain aspects of the disclosed embodiments.

For example, referring to FIGS. 8A and 8B, processor 110 may provide signals that control actuators 620a-620c via a cam to move (e.g., linearly), and cause the outer skin 840 of system 100 (apparatus 300) to deform in a manner that is simulates a breathing cycle controlled by the processes performed by processor 110. In one example, the slotted cam shown in FIG. 8A has spiral grooves like the cam shown in FIG. 7, which allow actuators 620a-620c to be moved in accordance with the controlled operations performed by processor 110. Other cam configurations are contemplated and are not limited to the cam shown in FIGS. 7, 8A and 8B.

As shown in FIG. 8A, at one point in the simulated breathing cycle (corresponding to a particular rotational position of the motor and thus a particular rotational position of the cam), actuators 620a and 620b, which move along a horizontal axis in the example orientation of FIG. 8A, are at a minimum distance from the cam (e.g., that are configured to simulate an inhalation stage of the simulated breathing cycle), and actuator 620c, which moves along a vertical axis in the example orientation of FIG. 8A, is at a maximum distance from the cam (e.g., that is configured to simulate the inhalation stage of the simulated breathing cycle). FIG. 8B shows positions of actuators 620a-620c during the exhalation stage of the simulated breathing cycle. For instance, as shown in FIG. 8B, actuators 620a and 620b are at their maximum distance from the cam, and actuator 620c is at its minimum distance from the cam. The exemplary slotted cam configuration shown in FIGS. 8A and 8B enables the motor of system 100 (and system 500 and apparatus 300) to be operated in one direction until a predetermined limit is reached, at which point system 100 may reverse operation of the motor to operate until another predetermined limit is reached, at which point the motor is again reversed. In this way, in certain embodiments, the process of operating the motor in cyclical reverse directions provides expansion and contraction of the outer skin 840 such that a realistic breathing cycle can be simulated for apparatus 300, e.g., the outer skin 840 moves in a manner that resembles mammalian contraction/expansion of the torso associated with breathing.

The relationship between the motor, cam, and actuators of the disclosed embodiments (e.g., as shown in FIGS. 8A and 8B, and also as described below in connection with FIGS. 9, 10A, 10B described below) achieves movement of the outer skin 840 that simulates the breathing cycle in a manner that maintains a fixed circumference of the outer skin (in a cross-sectional view such as the view of FIG. 8A) throughout the simulated breathing cycle. Thus, actuators 620a/620b move outwards (away from the cam) when actuator 620c moves inwards (toward the cam), and vice versa. As a result, the outer skin that may be implemented with the disclosed embodiments is expanded along a first dimension while simultaneously being contracted along another dimension, without being expanded at all directions at once. This feature of the disclosed embodiments provides an advantageous approach to simulated breathing that enables the use of outer skin material and related configurations that avoid unnecessary stretching while also providing a realistic breathing cycle simulation. Such features avoid issues that occur with systems that may include pumping air into a chamber surrounded by a skin, such that the skin expands in all directions simultaneously, subjecting the skin to stretching and possible bursting. The disclosed embodiments provide features such that outer skin 840 may be configured from less costly fabrics (e.g., material that is not needed to stretch in the way an expandable air chamber approach would require). Additionally, because excess fabric and/or gusset inserts are not needed to accommodate the expansion and contraction of the torso of the system and apparatus of the disclosed embodiments, the resulting simulated breathing provided by the configuration and operation of such embodiments may provide a more realistic, more user-friendly apparatus than other approaches.

Figure 9:
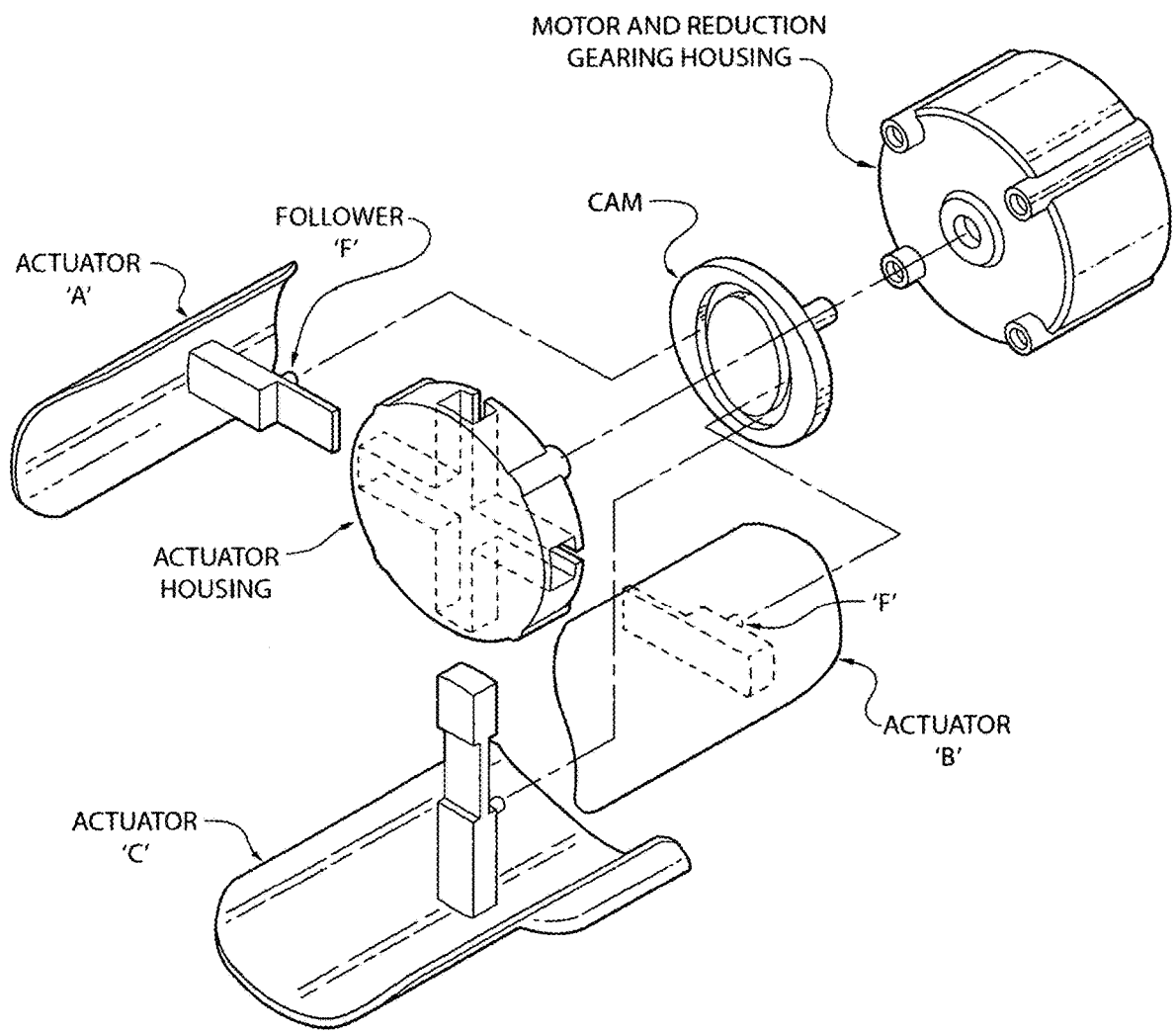
FIG. 9 shows a diagram of an exemplary exploded perspective view of an exemplary motorized, elliptical cam with actuators, consistent with certain aspects of the disclosed embodiments.

FIG. 9 is an exploded perspective view of an alternative cam and actuator configuration for system 100 (and system 500 and for use in apparatus 300) consistent with other embodiments. For instance, FIG. 9 shows a diagram of a configuration that uses an elliptical slotted cam instead of a spiral slotted cam as described above in connection with FIGS. 6A, 6B, and 7. Apart from the different type of cam and related configurations, the operation of components illustrated in FIG. 9 (and in FIGS. 10A-10B) is similar to those described above with respect to the spiral slotted cam implementations of the disclosed embodiments. Therefore, FIG. 9 is also illustrative of the features and configurations underlying the use of a motor and actuators for the system and apparatus discussed above in connection with FIGS. 6A and 6B, for example.

As shown in FIG. 9, the motor rotates an elliptical cam (CAM), e.g., via a reduction gearing. Actuators A, B, and C in this example may correspond to actuators described above in connection with the slotted cam embodiments, although the number and location of the actuators can vary. Followers F engage an elliptical cam groove, so the rotational motion of the cam causes the actuators (connected to respective followers F as shown in FIG. 9) to move linearly as the elliptical cam groove confines each follower F. An exemplary actuator housing for connecting to the actuators is also shown in FIG. 9, although other configurations for the actuator housing may be used.

The elliptical cam embodiment shown in FIG. 9 may provide features for system 100 (and system 500 and apparatus 300, with the configuration adjustments consistent with those of FIG. 9) such that reversal of the motor is not required at the end of each phase (inhalation or exhalation) of the respiration cycle. Rather, the motor can be operated continuously in one direction over multiple respiration cycles. This configuration reduces the complexity of the logic for controlling the motor (e.g., because a position need not be compared against a limit in order to determine that motor reversal is needed). Thus, the features provided by the embodiments of FIG. 9 may reduce cost of components and operational wear of components of the system and apparatus, and thus increase the expected lifetime of such components (e.g., because running the motor, gearing, and cam in only one direction reduces physical wear of the motor and associated components compared to running them in two directions with motor reversals as described above).

Figure 10A:
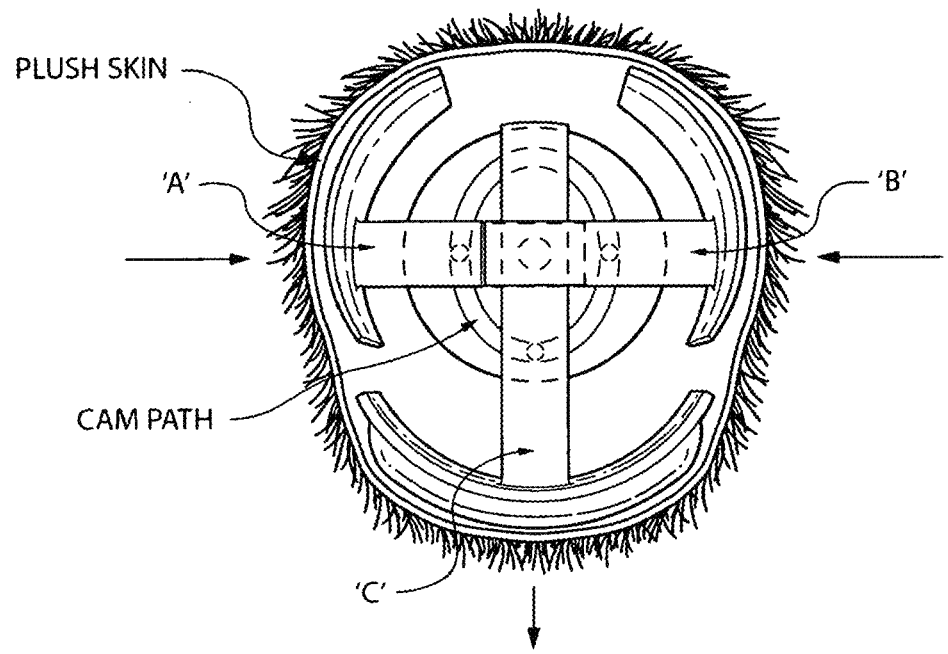
FIGS. 10A and 10B are cross-sectional views of different stages of a simulated breathing cycle in accordance with the elliptical cam embodiment depicted in FIG. 9, consistent with certain aspects of the disclosed embodiments.
Figure 10B:
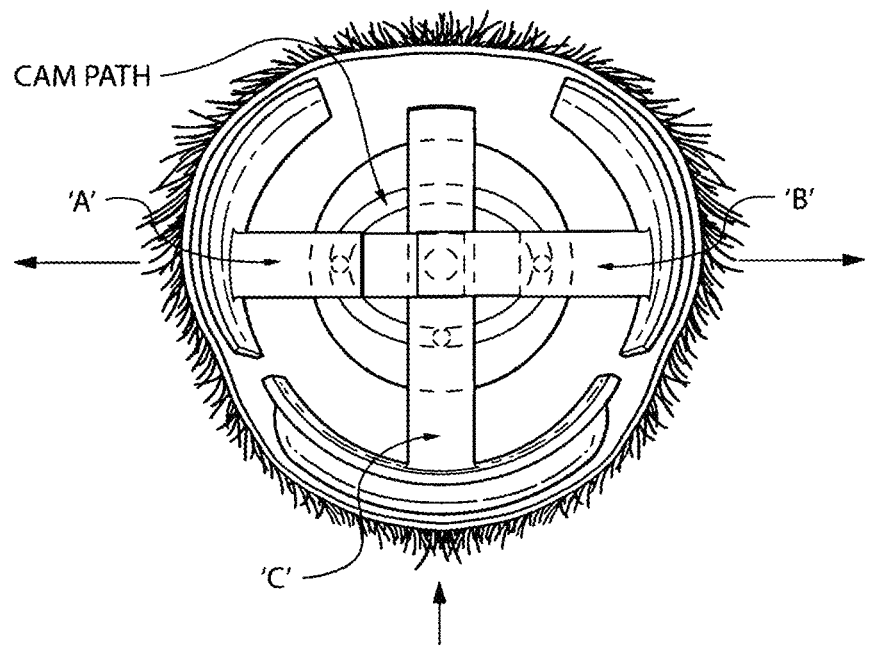

FIGS. 10A and 10B show cross-sectional views of the embodiment associated with that shown in FIG. 9, at different phases of the simulated breathing cycle. For example, FIG. 10A shows exemplary positions of the cam and its cam path in relation to actuators A', B' and C' that correspond to actuators A, B, and C shown in FIG. 9 during an inhalation phase of the simulated breathing cycle performed by aspects of the disclosed embodiments. FIG. 10B shows exemplary positions of the cam and its cam path in relation to actuators A', B' and C' (corresponding to actuators A, B, and C shown in FIG. 9) during an exhalation phase of the simulated breathing cycle performed by aspects of the disclosed embodiments. As shown in FIGS. 10A and 10B, the elliptical groove built into the cam confines followers F to lie within an ellipse that changes orientation as the cam rotates, translating the cam's rotational motion into linear displacement of each follower F (and thus of a corresponding actuator) relative to the cam.

Although aspects of the disclosed embodiments are described as being associated with data stored in memory and other tangible computer-readable storage mediums, one skilled in the art will appreciate that these aspects can also be stored on and executed from many types of non-transitory, tangible computer-readable media, such as secondary storage devices, like hard disks, floppy disks, or CD-ROM, or other forms of RAM or ROM. Accordingly, the disclosed implementations are not limited to the above described examples, in light of their full scope of equivalents.

Moreover, the disclosed embodiments are not limited to the configurations and operations described in the attached figures. Other aspects and functionalities may be implemented that provide one or more of the operations and features consistent with the disclosed embodiments. For example, in connection with embodiments associated with system 200 described in connection with FIG. 2, the disclosed embodiments may provide controlled operations that may adjust the operation of the components of system 100, system 500, and apparatus 300 as discussed above.

What is claimed is:

1. An respiratory regulation apparatus comprising:
   a CPU housing including a processor programmed to execute instructions to provide one or more control signals to control one or more components of the apparatus;
   a first actuator that includes a first actuator extension having a first follower;
   a second actuator that includes a second actuator extension having a second follower;
   an actuator housing that includes a first actuator housing receiving slot that receives the first actuator extension and a second actuator housing receiving slot that receives the second actuator extension; and
   a slotted cam that connects to a shaft of a motor that is configured to rotate the cam in a first rotational direction, the slotted cam including a continuous oval slot that receives the first follower and the second follower,
   the processor providing one or more of the control signals to control the rotational speed of the motor shaft such that the cam rotates in the first rotational direction at a first rotational speed that causes the first actuator extension to move inward and outward within the first actuator housing receiving slot in a repeating pattern at an actuator movement rate based on the rotational movement of the cam in the first rotational direction and the second actuator extension to move inward and outward within the second actuator housing receiving slot in a repeating pattern at the actuator movement rate based on the rotational movement of the cam in the first rotational direction,
   wherein the processor dynamically controls the rotational speed of the motor shaft such that the cam rotates in the first rotational direction at dynamically decreasing rotational speeds that result in the first and second actuators moving inward and outward within the respective first and second actuator housing receiving slots at dynamically decreasing actuator movement rates.

2. The respiratory regulation apparatus of claim 1, further comprising a third actuator including a third actuator extension having a third follower, wherein the actuator housing includes a third slot for receiving the third actuator extension.

3. The respiratory regulation apparatus of claim 2, wherein the cam oval slot receives the third follower.

4. The respiratory regulation apparatus of claim 3, wherein the actuator housing includes:
   a first groove that allows the first follower to move in a first linear direction within the actuator housing based on the rotation of the cam in the first rotational direction;
   a second groove that allows the second follower to move in a second linear direction within the actuator housing based on the rotation of the cam in the first rotational direction; and
   a third groove that allows the third follower to move in a third linear direction within the actuator housing based on the rotation of the cam in the first rotational direction.

5. The respiratory regulation toy apparatus of claim 4, wherein the first linear direction is a direction outward from the actuator housing, the second linear direction is a direction outward from the actuator housing, and the third linear direction is an inward direction toward the actuator housing.

6. The respiratory regulation toy apparatus of claim 5, wherein the apparatus is embedded within a plush animal toy that includes a torso that is expanded outward and contracted inward based on movement caused by the first, second, and third actuators in a manner that simulates breathing by the animal toy.

7. The respiratory regulation apparatus of claim 6, wherein the processor generates one or more of the control signals that dynamically control movement of the first, second, and third actuators in a dynamically adjustable pattern that simulates breathing of the toy animal.

8. The respiratory regulation apparatus of claim 5, wherein the torso is expanded outward on two opposing sides based on the movements of the first the second actuators by the rotation of the cam in the first rotational direction and, at the same time, the torso is contracted inward on a different torso side based on the movement of the third actuator by the rotation of the cam in the first rotational direction.

9. The respiratory regulation apparatus of claim 4, wherein the processor generates one or more of the control signals that dynamically control movement of the first, second, and third actuators in a dynamically adjustable pattern that simulates breathing.

10. The respiratory regulation apparatus of claim 1, wherein the apparatus is embedded within a plush animal toy that includes a torso that is expanded outward and contracted inward based on movement caused by the first and second actuators in a manner that simulates breathing by the animal toy.

11. The respiratory regulation apparatus of claim 1, further comprising movable apparatus leg extensions that connect to a body housing that includes the first and second actuators and cam, wherein the apparatus is embedded within a plush animal toy that includes extremities and the apparatus leg extensions form part of the animal toy extremities.

12. The respiratory regulation apparatus of claim 11, wherein at least one of the animal toy extremities resembles a prosthetic leg.

13. The respiratory regulation apparatus of claim 1, wherein the processor receives input signals reflecting a breathing pattern of an individual proximate to the apparatus and generates a control signal to control the motor to cause the cam to rotate at a first speed in the first rotational direction such that the first actuator extension moves inward and outward within the first actuator housing receiving slot at a first repeating pattern rate based on the rotational movement of the cam in the first rotational direction and such that the second actuator extension moves inward and outward within the second actuator housing receiving slot at the first repeating pattern rate based on the rotational movement of the cam in the first rotational direction.

14. The respiratory regulation apparatus of claim 13, wherein the processor generates subsequent control signals to control the motor to cause the cam to rotate at a dynamically decreasing speed in the first rotational direction such that the first actuator extension moves inward and outward within the first actuator housing receiving slot at a corresponding dynamic decreasing pattern rate based on the rotational movement of the cam in the first rotational direction and such that the second actuator extension moves inward and outward within the second actuator housing receiving slot at the corresponding dynamic decreasing pattern rate based on the rotational movement of the cam in the first rotational direction.

15. The respiratory regulation apparatus of claim 1, further comprising:
    an audio component for providing audio instructions through a speaker that reflect instructions regarding how to reduce a breathing rate to a calm level; and
    a lighting component that provides repeated lighting at a first lighting rate that is dynamically reduced based on a dynamic decrease in the rotational speed of the cam.

* * * * *